United States Patent [19]

Podraza

[11] Patent Number: 4,538,628
[45] Date of Patent: Sep. 3, 1985

[54] SMOKING COMPOSITIONS CONTAINING A DIOXANE DIESTER FLAVORANT-RELEASE ADDITIVE

[75] Inventor: Kenneth F. Podraza, Richmond, Va.

[73] Assignee: Philip Morris, Incorporated, New York, N.Y.

[21] Appl. No.: 659,464

[22] Filed: Oct. 10, 1984

[51] Int. Cl.$^3$ ............................................. A24B 15/40
[52] U.S. Cl. .................................................. 131/277
[58] Field of Search ................... 131/277, 278, 279; 549/379

[56] References Cited

U.S. PATENT DOCUMENTS 1,991,109  2/1935  McNally et al. .................. 549/379
2,164,356  7/1939  Slagh ................................. 549/379
2,186,359  1/1940  Britton et al. ..................... 549/379

Primary Examiner—Y. Harris Smith

[57] ABSTRACT

This invention provides smoking compositions which contain a dioxane diester compound as a flavorant additive.

In one of its embodiments, this invention provides tobacco compositions which contain a dioxane diester flavorant additive such as 2,5-bis(3-methylvaleryloxy)-1,4-dioxane:

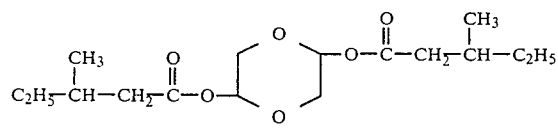

Under cigarette smoking conditions the above illustrated dioxane diester pyrolyzes into 3-methylvaleric acid and other products which enhance the flavor of the mainstream smoke and the aroma of sidestream smoke.

7 Claims, No Drawings

SMOKING COMPOSITIONS CONTAINING A DIOXANE DIESTER FLAVORANT-RELEASE ADDITIVE

BACKGROUND OF THE INVENTION

A variety of flavorants have been developed and proposed for incorporation into tobacco products. Illustrative of such tobacco flavorants are those described in U.S. Pat. Nos. 3,580,259; 3,625,224; 3,722,516; 3,750,674; 3,879,425; 3,881,025; 3,884,247; 3,890,981; 3,903,900; 3,914,451; 3,915,175; 3,920,027; 3,924,644; 3,937,228; 3,943,943; 3,586,387; 4,379,754; and the like.

The use of carboxylic acid flavorants for tobacco products has received acceptance because of the desirable aroma and flavor characteristics which they impart to the smoke (J. C. Leffingwell, H. J. Young, and E. Bernasek, "Tobacco Flavoring for Smoking Products," R. J. Reynolds Tobacco Company, Winston-Salem, 1972). Specifically, acetic acid is commonly used as an ingredient of a Latakia tobacco flavoring formulation (J. Merory, "Food Flavorings," AVI Publishing Company, Incorporated, Westport, Conn., page 420, 1968). Isovaleric acid and 3-methylvaleric acid are major ingredients in a Turkish tobacco flavor formulation described in U.S. Pat. No. 3,180,340. Desirable flavors have been imparted to cigarette smoke by the addition of 4-ketoacids to tobacco in the manner described in U.S. Pat. No. 3,313,307.

Numerous methods of adding flavorants to tobacco smoke are known. Typically the known methods suffer from one or more disadvantages, particularly when the flavorant is a low molecular weight carboxylic acid. Specifically, some of these acids are highly volatile and possess objectionably strong odors that render them difficult to use in bulk amounts required for manufacturing purposes. In addition, some of the volatile acids may impart an undesirable pack aroma.

In an attempt to alleviate some of these problems, carboxylic acids have been incorporated in tobacco as part of a compound (i.e., an organic acid release agent) in such form that upon burning of the tobacco the compound will liberate one or more organic acids imparting a selected and desired flavor and aroma to the smoke. While considerably more satisfactory than earlier attempts, even this technique has evidenced certain drawbacks.

U.S. Pat. No. 2,766,145 through U.S. Pat. No. 2,766,150 describe a variety of methods for treating tobacco with compounds that release carboxylic acids on pyrolysis. The U.S. Pat. No. 2,766,145 patent describes esters of monohydric and polyhydric compounds. The hydroxy compounds may be aliphatic or aromatic in nature.

The U.S. Pat. No. 2,766,146 patent describes esters of a sugar acid selected from aldonic acids and uronic acids. U.S. Pat. No. 2,766,150 describes nonvolatile synthetic polymers or condensation products, preferably those related to polyvinyl alcohol and vinyl alcohol-type condensation products. On pyrolysis, the carboxylic acid is liberated to flavor the smoke. These polymers have a distinct disadvantage in that they generally have high molecular weights and are more difficult to solubilize for application on tobacco.

Other patent references which disclose tobacco flavorant compositions that release carboxylic acids on pyrolysis include U.S. Pat. No. 4,036,237 and U.S. Pat. No. 4,171,702.

There is continuing research effort to develop improved low delivery smoking compositions which generate mainstream smoke with flavorant-enhanced taste and character under smoking conditions.

Accordingly, it is an object of this invention to provide smoking compositions having incorporated therein a flavorant component which is characterized by lack of mobility and/or volatility at ambient temperature.

It is another object of this invention to provide smoking tobacco compositions having incorporated therein a flavorant-release composition which under normal smoking conditions imparts improved flavor to mainstream smoke and improved aroma to sidestream smoke.

It is a further object of this invention to provide novel dioxane diester compositions which are adapted to be incorporated into tobacco compositions, and which under normal smoking conditions release a carboxylic acid type of volatile flavorant into cigarette smoke.

Other objects and advantages of the present invention shall become apparent from the following description and examples.

This patent application is related in subject matter to copending patent application Ser. No. 603,035, filed Apr. 23, 1984.

DESCRIPTION OF THE INVENTION

One or more objects of the present invention are accomplished by the provision of a smoking composition comprising an admixture of (1) combustible filler selected from natural tobacco, reconstituted tobacco and tobacco substitutes, and (2) between about 0.0001 and 2 weight percent, based on the total weight of filler, of a dioxane diester flavorant-release additive corresponding to the formula:

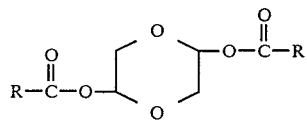

where R is a substituent selected from aliphatic, alicyclic and aromatic radicals.

In the ester formula represented above, the R substituent is one containing between about 1–12 carbon atoms, preferably between about 3–10 carbon atoms, such as propyl, methoxyethyl, butyl, isobutyl, pentyl, 2-hexyl, 5-hexenyl, cyclohexyl, cyclohexenyl, furfuryl, phenyl, tolyl, ethylphenyl, methoxyphenyl, ethoxyphenyl, hydroxyphenyl, naphthyl, and the like. In addition to carbon and hydrogen, the R substituent can contain heteroatoms such as oxygen, nitrogen and sulfur.

When a present invention smoking composition is subjected to normal smoking conditions such as with cigarettes, the dioxane ester additive decomposes to release a volatile pyrolysis carboxylic acid component (RCO$_2$H) which contributes flavor-enhancing properties to the mainstream smoke, such as for example:

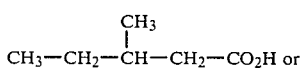

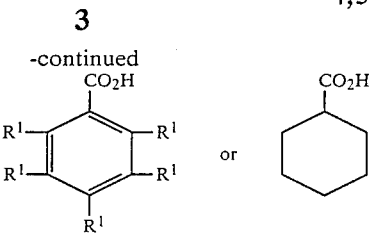

where $R^1$ is a substituent selected from hydrogen, alkyl, alkenyl, and alkoxy groups containing between about 1–4 carbon atoms.

Because of the diester structure, a high yield of carboxylic acid component is released from an invention dioxane diester under pyrolysis conditions. As noted previously, carboxylic acids are a known class of tobacco flavorants.

The present invention dioxane diesters are easily prepared and purified, and are soluble in organic solvents. They are uniquely stable and odorless compounds at ambient temperatures. In addition, the dioxane diesters decompose at a relatively low pyrolysis temperature (e.g., 200°–300° C.) to release a high yield of desirable flavor-enhancing components in mainstream smoke. The dioxane diesters are particularly effective for the efficient release of alkanoic acid flavorants such as butyric acid and isovaleric acid.

Preparation Of Dioxane Diesters

The dioxane diesters of the present invention can be prepared by reacting equivalent weights of a selected acyl halide compound with glycolaldehyde in the presence of a basic reagent such as pyridine or trimethylamine. The reaction may be visualized as proceeding via an in situ formed 2,5-dihydroxydioxane intermediate:

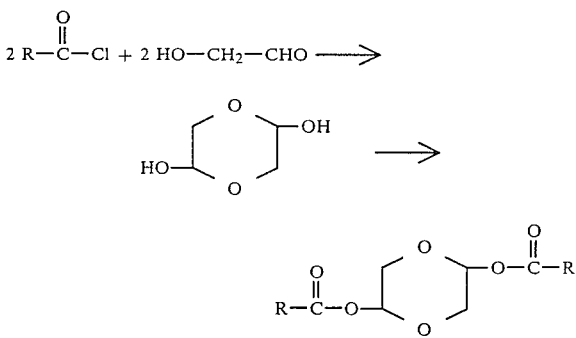

Details of synthesis methods for the preparation of substituted dioxanes are elaborated in prior art references. The synthesis of 2,5-diacetoxy-1,4-dioxane by the treatment of glycolaldehyde with acetic anhydride and pyridine is described in Berichte, 60, 1704(1927). The synthesis of 2,5-diacetoxy-1,4-dioxane by the reaction of 2,5-dichloro-1,4-dioxane with sodium acetate is disclosed in German Pat. No. 2,521,703 (Nov. 20, 1975).

The present invention dioxane diesters are readily amenable to crystallization and chromatographic purification procedures, as illustrated in the examples.

Preparation Of Tobacco Compositions

In a further embodiment, the present invention provides a method of preparing a smoking composition which is adapted to impart improved taste and character to mainstream smoke under smoking conditions, which method comprises incorporating into natural tobacco and/or reconstituted tobacco and/or tobacco substitute between about 0.0001 and 2 weight percent, based on composition weight, of a dioxane diester flavorant-release additive corresponding to the formula:

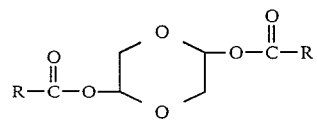

where R is a substituent selected from aliphatic, alicyclic and aromatic radicals containing between about 3–10 carbon atoms.

The invention dioxane diester flavorant-release additive can be incorporated into the tobacco in accordance with methods known and used in the art. Preferably the flavorant-release additive is dissolved in a solvent such as alcohol or aqueous alcohol and then sprayed or injected into the tobacco and/or tobacco substitute matrix. Such method ensures an even distribution of the flavorant additive throughout the filler, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or tobacco substitute filler in a concentration between about 0.5–5 weight percent, based on the weight of filler, and then subsequently to blend the treated filler with filler which does not contain flavorant additive.

The term "tobacco substitute" is meant to include non-tobacco smoking filler materials such as are disclosed in U.S. Pat. Nos. 3,703,177; 3,796,222; 4,019,521; 4,079,742; and references cited therein, incorporated herein by reference.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formation of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the hulls may be handled and used similarly to a tobacco product.

U.S. Pat. No. 4,019,521 discloses a process for forming a smoking material which involves heating a cellulosic or carbohydrate material at a temperature of 150°–750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

The following Examples are further illustrative of the present invention. The specific ingredients and processing parameters are presented as being typical, and various modifications can be derived in view of the foregoing disclosure within the scope of the invention.

Examples I–IV illustrate the preparation of dioxane diester compounds in accordance with the present invention. Infrared and nuclear magnetic resonance analyses are utilized to confirm the structure of each compound.

As shown in Example VI, when a present invention dioxane diester is incorporated into low delivery filtered cigarette tobacco filler, there is a detectable enhancement of flavor and body in the mainstream smoke as compared to control cigarettes not containing a dioxane diester flavorant-release additive.

EXAMPLE 1

2,5-Bis(3-methylvaleryloxy)-1,4-dioxane

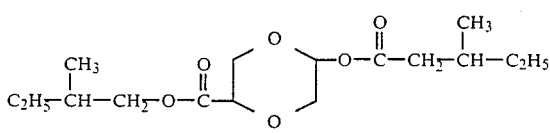

To a solution of 2.5 ml of pyridine in 50 ml of methylene chloride is added with stirring 1.0 g (0.0167 mole) of glycolaldehyde. The resulting suspension is chilled in an ice bath. A solution of 2.25 g (0.0167 mole) of 3-methylvaleryl chloride in 10 ml of methylene chloride is added dropwise. Stirring is continued for approximately 15 minutes while maintaining the temperature at 0° C., then 18–24 hours at room temperature. The reaction mixture is washed with water, and then with aqueous saturated sodium bicarbonate. The organic layer is dried over sodium sulfate.

Evaporation of the solvent under reduced pressure yields a residue, to which toluene is added and removed by evaporation under reduced pressure. The semi-solid obtained is purified by preparative thin layer chromatography on silica gel using chloroform as the eluent, yielding 1.8 g of the pure product, m.p. 71°–72° C.

NMR and IR data confirm the above structure.

Anal. calc. for $C_{16}H_{28}O_6$: C,60.74; H,8.92. Found: C,60.89; H,8.85.

EXAMPLE II 2,5-Bis(isovaleryloxy)-1,4-dioxane

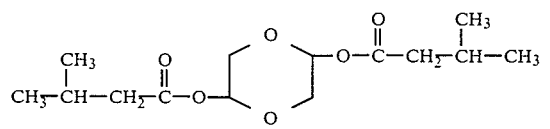

The synthesis of 2,5-bis(isovaleryloxy)-1,4-dioxane is conducted on a 0.0167 mole scale with the appropriate acyl chloride and employing the same conditions as described in Example I, except that the semi-solid is purified by recrystallization from hexane. A 1.6 g yield of the pure product is obtained, m.p. 104°–105° C.

NMR and IR data confirm the above structure.

Anal. calc. for $C_{14}H_{24}O_6$: C,58.32; H,8.39. Found: C,58.53; H,8.30.

EXAMPLE III 2,5-Bis(cyclohexylcarbonyloxy)-1,4-dioxane

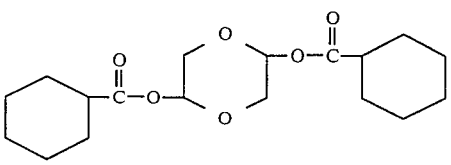

The synthesis of 2,5-bis(cyclohexylcarbonyloxy)-1,4-dioxane is conducted on a 0.0167 mole scale with the appropriate acyl chloride and employing the same conditions as described in Example I, except that the semi-solid is purified by recrystallization from hexane. A 1.1 g yield of the pure product is obtained, m.p. 156°–158° C.

NMR and IR data confirm the above structure.

Anal. calc. for $C_{18}H_{28}O_6$: C,63.51; H,8.29. Found: C,63.76; H,8.49.

EXAMPLE IV 2,5-Bis(benzoyloxy)-1,4-dioxane

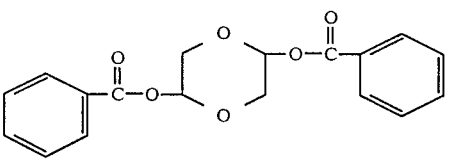

The synthesis of 2,5-bis(benzoyloxy)-1,4-dioxane is conducted on a 0.0167 mole scale with the appropriate acyl chloride and employing the same conditions as described in Example I, except that the semi-solid is purified by recrystallization from chloroform/hexane. A 0.5 g yield of the pure product is obtained, m.p. 187°–189° C.

NMR and IR data confirm the above structure.

Anal. calc. for $C_{18}H_{16}O_6$: C,65.85; H,4.91. Found: C,65.67; H,4.93.

EXAMPLE V

This Example illustrates the pyrolysis of present invention diesters of 2,5-dihydroxy-1,4-dioxane to yield carboxylic acid flavorants.

A 50 mg sample of each of 2,5-bis(3-methylvaleryloxy)-1,4-dioxane(I) and 2,5-bis(isovaleryloxy)-1,4-dioxane(II) are pyrolyzed in a tube at 250° C. for 10 minutes. The yield of the released carboxylic acid component in each case is determined by GC.

| Compound | Flavorant | Yield % |
| --- | --- | --- |
| I | 3-methylvaleric acid | 50 |
| II | isovaleric acid | 50 |

In a similar manner, under pyrolysis conditions 2,5-bis(cyclohexylcarbonyloxy)-1,4-dioxane releases cyclohexanecarboxylic acid and 2,5-bis(benzoyloxy)-1,4-dioxane releases benzoic acid.

EXAMPLE VI

An ethanolic solution of 2,5-bis(3-methylvaleryloxy)-1,4-dioxane is sprayed on tobacco filler to provide a final concentration of 0.2% by weight of the tobacco.

Cigarettes are fabricated employing both treated and untreated filler (control). The cigarettes are equipped with conventional cellulose acetate fillers, and are designed to deliver approximately 5–6 mg TPM (tar).

The control and treated cigarettes are smoked by a panel of experienced smokers. The diester treated cigarettes are found to have a sweeter, increased sour-solvating response as compared to the untreated controls.

What is claimed is:

1. A smoking composition comprising an admixture of (1) combustible filler selected from natural tobacco, reconstituted tobacco and tobacco substitutes, and (2) between about 0.0001 and 2 weight percent, based on the total weight of filler, of a dioxane diester flavorant-release additive corresponding to the formula:

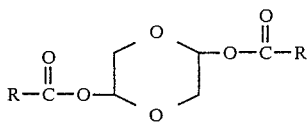

where R is a substituent selected from aliphatic, alicyclic, aromatic and substitued aromatic radicals containing between about 1–12 carbon atoms.

2. A smoking composition in accordance with claim 1 wherein the tobacco substitutes are selected from pectinaceous cellulosic and other carbohydrate materials.

3. A smoking composition in accordance with claim 1 wherein the diester flavorant is 2,5-bis(3-methylvaleryloxy)-1,4-dioxane.

4. A smoking composition in accordance with claim 1 wherein the diester flavorant is 2,5-bis(isovaleryloxy)-1,4-dioxane.

5. A smoking composition in accordance with claim 1 wherein the diester flavorant is 2,5-bis(cyclohexylcarbonyloxy)-1,4-dioxane.

6. A smoking composition in accordance with claim 1 wherein the diester flavorant is 2,5-bis(benzoyloxy)-1,4-dioxane.

7. A method of preparing a smoking composition which is adapted to impart flavoring to the mainstream and sidestream smoke under smoking conditions, which method comprises incorporating into natural tobacco, reconstituted tobacco or tobacco substitute between about 0.0001 and 2 weight percent, based on composition weight, of a dioxane diester flavorant-release additive corresponding to the formula:

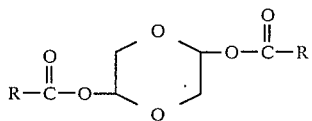

where R is a substituent selected from aliphatic, alicyclic and aromatic radicals.

* * * * *